June 10, 1969 R. M. BODLEY Plant Pat. 2,893
ROSE PLANT
Filed Aug. 7, 1967
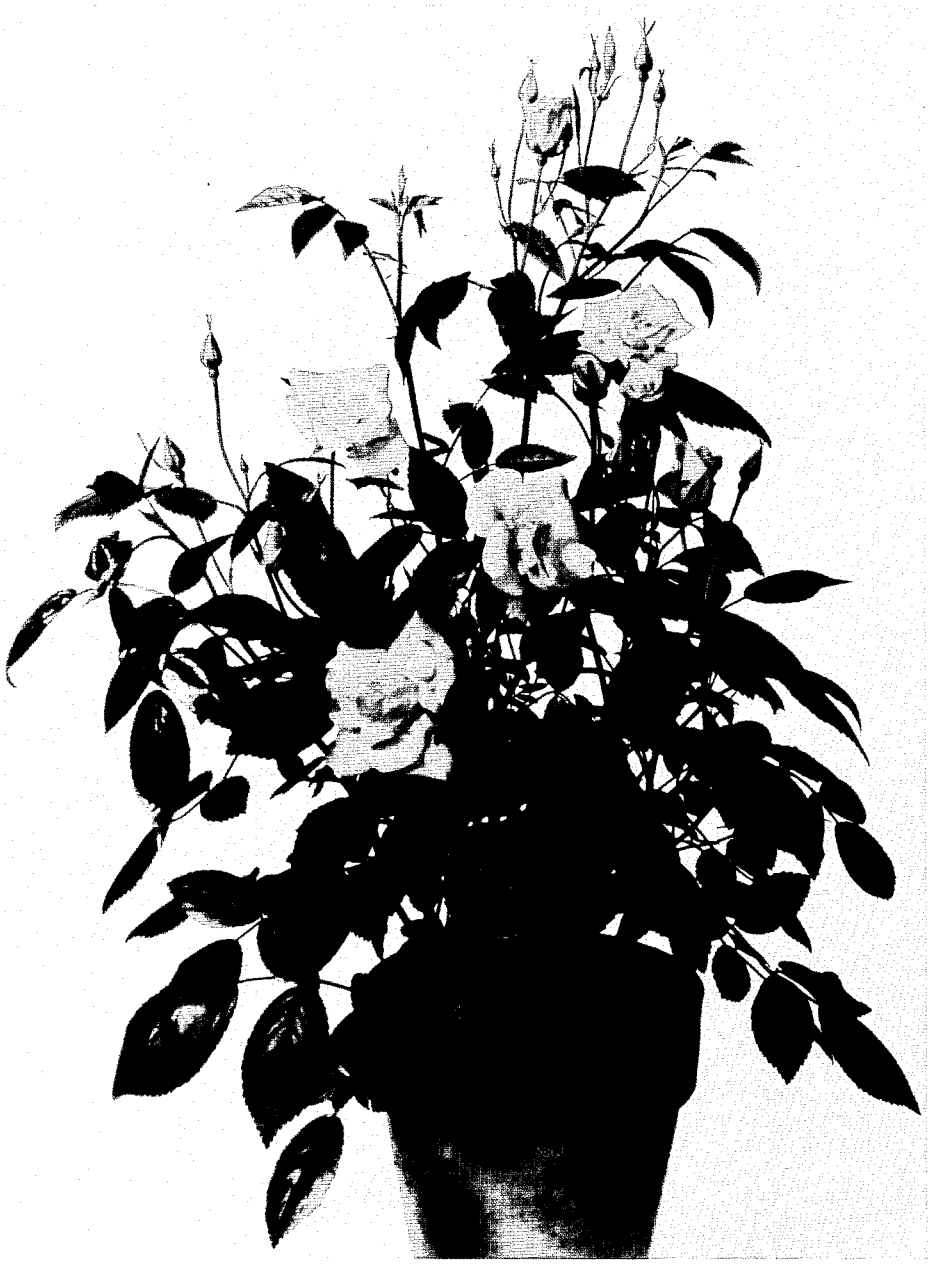
ROYDEN M. BODLEY
INVENTOR
BY
BUCKHORN, BLORE, KLARQUIST & SPARKMAN
ATTORNEYS United States Patent Office Plant Pat. 2,893
Patented June 10, 1969

2,893
ROSE PLANT
Royden M. Bodley, 4605 SE. Powell Blvd.,
Portland, Oreg. 97206
Filed Aug. 7, 1967, Ser. No. 658,966
Int. Cl. A01h 5/02
U.S. Cl. Plt.—27 1 Claim The present invention relates to a new and distinct variety of rose plant of the polyantha class, and more specifically to a seedling of a rose plant of unknown derivation. The seed parent was given to me in 1955 and subsequently grown by me in my nursery at 4605 SE. Powell Blvd., Portland, Oreg., next to a dark pink sport of a Rita Sammons rose which is believed to be the pollen parent. The Rita Sammons rose is an unpatented variety.

Seeds produced by the seed parent in 1963 were planted by me in January 1964 in my said nursery. In June 1964, while inspecting in my nursery the seedlings resulting from such planting, I discovered one seedling (my new variety) that had flowers of a distinctly different color from those of the seed parent or pollen parent in that the flowers were a red or very deep pink and occasionally striped with white, whereas the flowers of the seed and pollen parents are of ordinary pink color. Subsequently I discovered further unusual characteristics of my new variety, and particularly noted (1) an abundance of buds and flowers in excess of those produced by the seed and pollen parents; (2) an ability of my variety to reproduce easily and successfully by cuttings set in sand beds, to a degree greatly in excess of that possessed by the seed and pollen parents; and (3) the ability of my new variety to grow in pots for substantial periods of time, considerably in excess of that possessed by the pollen and seed parents. The latter characteristic makes my rose particularly desirable as a house plant for apartment dwellers, for use on patios, lanais, sun decks, etc.

The drawing is a reproduction of a colored photograph of a bush of my invention which was grown from a cutting.

I personally first asexually reproduced my new variety by taking cuttings from the original plant and planting these in sand beds. I have found great success in reproducing my plant by cuttings if the cuttings are taken from greenhouse plants under mild temperature conditions (say roughly 56° to 66° F.) and from light, thin wood, say ¾ inch to 1½ inches in length, and 1/16 to ¼ inch in diameter. Under these circumstances, the success in reproduction from cuttings has been very high, up to 98% success, and rarely below 90%. Larger cuttings do not root as soon or as easily, and cuttings taken from field grown plants do not root as well. With cuttings from field grown plants, the degree of success has been around 50 to 60%.

In view of my success in reproduction by cuttings I have found it unnecessary to reproduce the new variety by budding because the bushes produced from cuttings are free from the heavy stock which is incident to reproduction by budding.

After the rooting occurred, I place the rooted cuttings in small pots, say 2" pots for about a month, then transplant them to larger pots, say 4" pots, where they bloom in about three to four months after having been transplanted. If plants from the four inch pots are planted in the field in January in five or six inch pots, they will make nice bushy plants for Mother's Day. My plants make lots of foliage, enough to hide the pots, and when properly grown are around 15 inches tall and have a spread of around 15 inches. Ideally they should be grown in a cool or mild climate, say 50° at night and around 60° during the daytime.

I have reproduced my plant by way of cuttings, not only from the original plant, but from bushes grown from cuttings, and my new rose variety has proved to hold its distinguishing characteristics through succeeding propagation by cuttings, and the characteristics of my bush have proved fixed.

In regard to the seed parent, I feel quite certain that it is a floribunda. It has flowers about 3½ inches in diameter, with flat petals, the flowers not being very double, with about two rows of petals, and perhaps a few more petals than my inventive rose. When the petals first open they have the luminous sheen that is characteristic of my inventive rose, the color of the petals being medium soft pink in contrast to the deeper color of my inventive rose. The leaves of the seed parent are more oval than those of my inventive rose, and there are usually five leaflets on the seed parent. Also, there are usually three or four buds or flowers to a stalk on the seed parent, which is considerably fewer than those on the stalk of my inventive rose.

The budding of my new variety is very substantial and considerably in excess of the budding produced on the seed and pollen parents. There may be 150 buds on one of my bushes at any one time, and my bush is a very free bloomer and it is not unusual to find as many as 36 buds on one stem. The buds in practically every instance are perfectly formed and produce flowers which are not too double, with petals which are relatively flat. The flowers stay full three weeks or more, and fall clean with the number of petals varying from about 15 to 30 in two or three rows of petals, with the average number of petals being from 15 to 20. The growth of my plant is substantial and the plant will grow from 18 to 20 inches in one year in the field. The stock of my rose bush is wiry, slender and strong. The foliage is heavy and frequently covers the pot in which it is grown.

The flowers of my bush turn purple when they wither, whereas the Rita Sammons flowers turn blue. Excessive heat will adversely affect potted plants more than plants in beds or in the field, and the color under excessive heat circumstances when the plants are potted tends to fade to pink.

The following is a detailed description of my new variety with color terminology following that of the R.H.S. Color Chart of the Royal Horticultural Society, except where ordinary dictionary significance of color is indicated.

Location where observations were made and all activities referred to in this specification occurred: 4605 SE. Powell Blvd., Portland, Oreg., field and greenhouse.

Blooming habit:
- *Blooms.*—Profusely.
- *Recurrent.*—Continuous.

*Flower*

Bud:
- *Size.*—Small.
- *Form.*—Long, pointed.
- *Color.*—When sepals first divide—57C. When petals begin to unfurl—57B. When half grown—57B. Inside of petals—57D. Reverse of petals—58B.
- *Sepals.*—Smooth edge. Curl back when half open.
- *Calyx.*—Shape—pear shaped. Size—small, slender. Aspect—smooth.
- *Peduncle.*—Length—long. Aspect—smooth. Color—light green. Strength—erect, slender.
- *Opening.*—Opens well—affected by adverse conditions.

Bloom:
- *Size.*—Small—2–2½" diameter. Center of flower does not show until fully open.
- *Borne.*—Together, in clusters (flat).
- *Stems.*—Medium, strong.
- *Form.*—When first open flat. Permanent—flattens, outer petals curl back.

*Petalage.*—Semi-single. Number of petals under normal conditions—15–25.

*Color.*—Flower has luminuous glow when first opening. Carmine washed with sulphur yellow. Center of flower—open 58B. Inside of petals—57D. Reverse of petals—58B. General tonality from distance—63B.

*Variegations if any.*—Striped—pale yellow turning white occasionally down center, blotched.

*Discoloration.*—Tonality at end of first day—luminous glow. Second day—loses glow—58C. Third day—63C.

Petals:

*Texture.*—Thin, soft. Fades in hot weather.

*Appearance.*—Satiny inside, velvety outside.

*Form.*—Oval, slightly notched.

*Arrangement.*—Informal (with rags in center).

*Petaloids in center.*—Few, small.

*Persistence.*—Drop off cleanly.

*Fragrance.*—Slight, "Old Rose perfume."

*Lastingness.*—On the plant—long. As cut flower—long.

Sexual organs:

*Stamens, anthers.*—Small, many, yellow.

*Arrangement.*—Regular around styles.

*Stamens, filaments.*—Medium, pale yellow.

*Pollen.*—Lemon yellow.

*Styles.*—Loosely separated, even, medium, thin.

*Stigma.*—Yellow.

*Ovaries.*—All enclosed in calyx.

Fruit:

*Form.*—Round.

*Aspect.*—Smooth.

*Sepals.*—Caducous (soon falling).

*Plant*

Form: Bush.

Growth: Medium, branching.

Foliage: 5 leaflets—sometimes 7.

*Size.*—Medium.

*Quantity.*—Abundant.

*Color.*—Normal green (upper side)—new foliage. Normal green (upper side)—old foliage. Light green (under side)—old foliage.

*Shape.*—Oval pointed.

*Texture.*—Upper side—smooth, flat. Under side—smooth.

*Ribs and veins.*—Ordinary.

*Edge.*—Serrated.

*Serration.*—Single.

*Leaf stem.*—Green—under side, prickles.

*Stipules.*—Medium, serrated.

*Disease resistance.*—Susceptible to mildew.

Wood:

*New wood.*—Reddish. Bark smooth.

*Old wood.*—Green. Bark smooth.

Thorns:

*Quantity.*—On main stalks from base—few. On laterals from stalk—few.

*Form.*—Narrow base, medium, straight.

*Color when young.*—Green and red.

*Position.*—Irregular, sometimes in pairs.

*Prickles.*—Quantity: on main stalks—none; on laterals—none.

*Short needles.*—Quantity: on main stalks—none; on laterals—none.

I claim:

1. A new and distinct variety of rose plant of the polyantha class as herein shown and described, characterized particularly as to novelty by its red or deep pink flower color, by its vigorous growth habits, its ability to reproduce rapidly and successfully by cuttings, and its ability to grow well in pots for extended periods of time.

No references cited.

ROBERT E. BAGWILL, *Primary Examiner.*